United States Patent
Liu et al.

(10) Patent No.: US 10,234,521 B2
(45) Date of Patent: Mar. 19, 2019

(54) SYSTEMS AND METHODS FOR FIELD MAPPING IN MAGNETIC RESONANCE IMAGING

(71) Applicants: Junmin Liu, London (CA); Maria Drangova, London (CA)

(72) Inventors: Junmin Liu, London (CA); Maria Drangova, London (CA)

(*) Notice: Subject to any disclaimer, the term of this patent is extended or adjusted under 35 U.S.C. 154(b) by 310 days.

(21) Appl. No.: 15/304,741

(22) PCT Filed: Apr. 24, 2015

(86) PCT No.: PCT/CA2015/050344
§ 371 (c)(1),
(2) Date: Oct. 17, 2016

(87) PCT Pub. No.: WO2015/161386
PCT Pub. Date: Oct. 29, 2015

(65) Prior Publication Data
US 2017/0038446 A1 Feb. 9, 2017

Related U.S. Application Data

(60) Provisional application No. 61/983,946, filed on Apr. 24, 2014.

(51) Int. Cl.
*G01R 33/24* (2006.01)
*G01R 33/44* (2006.01)
(Continued)

(52) U.S. Cl.
CPC ............ *G01R 33/443* (2013.01); *A61B 5/055* (2013.01); *A61B 5/4872* (2013.01);
(Continued)

(58) Field of Classification Search
CPC .... A61B 5/055; A61B 5/4872; G01R 33/443; G01R 33/243; G01R 33/4828; G01R 33/56563; G01R 33/50
(Continued)

(56) References Cited

U.S. PATENT DOCUMENTS

| | | | |
|---|---|---|---|
| 7,116,105 B1 * | 10/2006 | Zhang | G01R 33/5613 324/307 |
| 8,138,759 B2 * | 3/2012 | Greiser | G01R 33/3875 324/309 |

(Continued)

FOREIGN PATENT DOCUMENTS

| | | | | |
|---|---|---|---|---|
| CN | 103513202 | | 1/2014 | |
| JP | 2016041384 A | * | 3/2016 | ......... G01R 33/4828 |
| WO | 2015028481 | | 3/2015 | |

OTHER PUBLICATIONS

Dymerska et al., A method for the dynamic correction of B0-related distortions in single-echo EPI at 7 T. NeuroImage 168 (2018) 321-331. /& 2018 The Authors. Published by Elsevier Inc. (Year: 2018).*

(Continued)

*Primary Examiner* — Patrick Assouad
*Assistant Examiner* — Sean Curtis
(74) *Attorney, Agent, or Firm* — Hill & Schumacher

(57) ABSTRACT

Various embodiments of the present disclosure present unwrapping based B0 mapping systems and methods. An initial B0 map is obtained by unwrapping a pseudo-in-phase complex data that is generated from selected echoes of multi-echo gradient echo image data. Global and local phase errors that are present in the initial B0 map are corrected to produce a phase-error-corrected B0 map. A bias frequency shift is employed to produce a corrected fat-fraction map (Continued)

based on the phase-error-corrected B0 map. The corrected fat-fraction map is employed to generate a final B0 map.

24 Claims, 11 Drawing Sheets

(51) Int. Cl.
*G01R 33/565* (2006.01)
*A61B 5/055* (2006.01)
*G01R 33/48* (2006.01)
*A61B 5/00* (2006.01)
*G01R 33/50* (2006.01)

(52) U.S. Cl.
CPC ....... *G01R 33/243* (2013.01); *G01R 33/4828* (2013.01); *G01R 33/56563* (2013.01); *G01R 33/50* (2013.01)

(58) Field of Classification Search
USPC .................................................. 324/300–322
See application file for complete search history.

(56) References Cited

U.S. PATENT DOCUMENTS

| | | | | |
|---|---|---|---|---|
| 8,311,609 | B2* | 11/2012 | Harvey | G01R 33/4804 600/410 |
| 8,781,197 | B2* | 7/2014 | Wang | G01R 33/54 382/131 |
| 9,329,250 | B2* | 5/2016 | Taviani | G01R 33/4828 |
| 9,714,999 | B1* | 7/2017 | Nakai | G01R 33/4828 |
| 9,943,246 | B2* | 4/2018 | Reeder | A61B 5/055 |
| 2008/0287773 | A1* | 11/2008 | Harvey | G01R 33/4804 600/412 |
| 2010/0127702 | A1* | 5/2010 | Greiser | G01R 33/3875 324/309 |
| 2011/0044524 | A1* | 2/2011 | Wang | G01R 33/54 382/131 |
| 2013/0214781 | A1* | 8/2013 | Hernando | G01R 33/4828 324/309 |
| 2014/0142417 | A1* | 5/2014 | Reeder | A61B 5/055 600/420 |
| 2014/0266192 | A1* | 9/2014 | Taviani | G01R 33/4828 324/309 |
| 2017/0038446 | A1* | 2/2017 | Liu | A61B 5/4872 |
| 2017/0192075 | A1* | 7/2017 | Nakai | G01R 33/4828 |
| 2017/0322274 | A1* | 11/2017 | Bolster, Jr. | G01R 33/5615 |
| 2018/0210056 | A1* | 7/2018 | Koehler | G01R 33/5607 |

OTHER PUBLICATIONS

Wu et al., Accurate B0 mapping with an adaptive algorithm integrating KESA, PRELUDE, and time-domain phase unwrapping. Proc . Intl. Soc. Mag. Reson. Med. 20 (2012) (Year: 2012).*
Liu et al., Method of B0 Mapping With Magnitude-Based Correction for Bipolar Two-Point Dixon Cardiac MRI. Magnetic Resonance in Medicine 78:1862-1869 (2017) (Year: 2017).*
A Matakos et al.,Estimation of geometrically undistorted B0 inhomogeneity maps.Phys. Med. Biol. 59 (2014) 4945-4959. (Year: 2014).*
Simon et al., B0 Mapping With Multi-Channel RF Coils at High Field. Magnetic Resonance in Medicine 66:976-988 (2011) (Year: 2011).*
Matakos et al., A Robust Method for Estimating B0 Inhomogeneity Field in the Liver by Mitigating Fat Signals and Phase-Wrapping. tomography.org | vol. 3 No. 2 | Jun. 2017 (Year: 2017).*
Rydell et al., Proccedings of International Conference on Medical Image Computing and Computer-Assisted Intervention (MICCAI'07), 2007.
Cusack et al., NeuroImage 16, 754-764, 2002.
Block et al., Proc. Intl. Soc. Mag. Reson. Med. 19, 2011.
Bergland, J. Separation of Water and Fat Signal in Magnetic Resonance Imaging, Thesis, Uppsala University, 2011.
Pauly, J. Dixon Reconstruction (Course Notes), 2005.
Yu et al., Magn Reson Med. November ; 60(5): 1122-1134, 2008.
Baselice et al., Sensors 10, 266-279, 2010.
Yu et al., Magnetic Resonance in Medicine 67:1065-1076, 2012.
Yu et al., magnetic Resonance in Medicine 66:199-206, 2011.
Cui et al., Magn Reson Med, 73: 1289-199.doi: 10.1002/mrm. 25193, Mar. 6, 2014.
Hernando et al., Magn Reson Med, 59:571-580. Doi: 10.1002/mrm21522, Feb. 27, 2008.
Reeder et al., Magn Reson Med, 54:636-644 doi: 10-1002/mrm. 20624, Aug. 9, 2005.
Liu et al., Magn Reson Med. doi: 10.1002/mrm.25497, Oct. 28, 2014.
Written Opinion in related PCT Application No. PCT/CA2015/050344, dated Aug. 20, 2015.
International Search Report in related PCT Application No. PCT/CA2015/050344, dated Aug. 20, 2015.

* cited by examiner

SYSTEMS AND METHODS FOR FIELD MAPPING IN MAGNETIC RESONANCE IMAGING

CROSS-REFERENCE TO RELATED APPLICATION

This application is a National Phase application claiming the benefit of the international PCT Patent Application No. PCT/CA2015/050344, filed on Apr. 25, 2015, in English, which claims priority to U.S. Provisional Application No. 61/983,946, titled "Method for Field Mapping" and filed on Apr. 24, 2014, the entire contents of which are incorporated herein by reference.

BACKGROUND

The present disclosure relates to magnetic resonance (MR) imaging. More particularly, the present disclosure relates to methods of estimating and mapping the main magnetic field (B0), where B0 inhomogeneity is introduced when a body is placed in a MR scanner.

An accurate B0 off-resonance map has many applications, such as in shimming, image distortion correction, quantitative susceptibility mapping and fat/water separation. However, accurate estimation of the B0 map can be hampered by the additional phase term related to the chemical shift of fat (1). To avoid the effect of chemical shift, conventional B0 mapping is performed by phase unwrapping of the complex data where signals from fat and water are "in-phase", which is ensured by using a single-peak model for both water and fat, e.g. 3-point Dixon technique (2,3).

Recently, multi-echo gradient echo (GRE) acquisition has attracted the attention of the academic community because of its potential for performing R2* (decay rate) mapping, B0 mapping, quantitative fat/water separation and quantitative susceptibility mapping from a single scan. Many multi-point Dixon techniques (1,4,5) have been established to quantify fat-fraction (FF) through iterative multi-parameter fitting procedures by using a multi-peak fat model, where the fitting parameters include the frequency shift ($f_{b0}$) due to B0 inhomogeneity, the signals of the water ($\rho_W$) and fat ($\rho_F$) components, and $R_2^*$. The results of the iterative procedure on a voxel-by-voxel basis (6) can be further enhanced using region-growing (7), region-merging (8), region-labeling (9), fat likelihood analysis (10), applying a multi-resolution strategy for guiding the search process (11,12), and algebraic decomposition (13). The state of the art is to estimate the aforementioned multi-parameters jointly for all voxels by using the graph-cut algorithm in B0 map estimation (4, 14-16).

The multi-point Dixon techniques mainly aim to generate an accurate FF map instead of a realistic and accurate B0 map. To improve the robustness for preventing fat/water swaps, most of these techniques apply two constraints during the B0 searching process: the prior knowledge of spatial smoothness and a limited range of $f_{b0}$ values. Because the effect of the phase term in the complex signal equation is periodic, an accurate FF measurement can be achieved from either "non-smooth" (9) or "over smooth" (8) B0 maps. Further, if the true B0 inhomogeneity is outside the range, the resulting B0 map will be wrapped and might not be useful for further data processing.

SUMMARY

Various embodiments of the present disclosure present unwrapping based B0 mapping systems and methods. An initial B0 map is obtained by unwrapping a pseudo-in-phase complex data that is generated from selected echoes of multi-echo gradient echo image data. Global and local phase errors that are present in the initial B0 map are corrected to produce a phase-error-corrected B0 map. A bias frequency shift is employed to produce a corrected fat-fraction map based on the phase-error-corrected B0 map. The corrected fat-fraction map is employed to generate a final B0 map.

Accordingly, in a first aspect, there is provided a method of mapping of the main magnetic field (B0) of a magnetic resonance scanner, the method comprising:

receiving multiple gradient echo image data;

processing the multiple gradient echo image data to generate a magnitude-based water mask;

generating a complex data set based on selected echoes of the multiple gradient echo image data, wherein the selected echoes are selected to have an effective echo delay time that corresponds to a fat-induced phase shift that is closest to a multiple of 2*pi;

unwrapping the phase of the complex data set to obtain an initial B0 map;

calculating a bias frequency shift based on a calculated phase shift of fat during acquisition of the selected echoes and the effective echo time;

calculating a bias-corrected phase shift of fat that is produced during acquisition of the selected echoes;

employing the magnitude-based water mask to correct for a global phase error present in the initial B0 map, thereby obtaining a globally phase-error-corrected B0 map;

employing the bias-corrected phase shift of fat to correct for local phase errors in the globally phase-error-corrected B0 map, thereby obtaining a phase-error corrected B0 map;

calculating a corrected fat-fraction map based on the phase-error corrected B0 map and the bias frequency shift; and employing the corrected fat-fraction map to perform bias removal on the phase-error corrected B0 map and generating a final B0 frequency map.

In another aspect, there is provided a method of mapping of the main magnetic field (B0) of a magnetic resonance scanner, the method comprising:

receiving multiple gradient echo image data;

processing the multiple gradient echo image data to generate a magnitude-based water mask;

generating a complex data set based on selected echoes of the multiple gradient echo image data, wherein the selected echoes are selected to have an effective echo delay time that corresponds to a fat-induced phase shift that is closest to a multiple of 2*pi;

unwrapping the phase of the complex data set to obtain an initial B0 map;

employing the magnitude-based water mask to correct for a global phase error present in the initial B0 map, thereby obtaining a globally phase-error-corrected B0 map;

employing a bias-corrected phase shift of fat to correct for local phase errors in the globally phase-error-corrected B0 map, thereby obtaining a phase-error corrected B0 map;

calculating a corrected fat-fraction map based on the phase-error corrected B0 map and a bias frequency shift; and employing the corrected fat-fraction map to perform bias removal on the phase-error corrected B0 map and generating a final B0 frequency map.

In another aspect, there is provided a method of mapping of the main magnetic field (B0) of a magnetic resonance scanner, the method comprising:

receiving multiple gradient echo image data;

generating a complex data set based on selected echoes of the multiple gradient echo image data, wherein the selected echoes are selected to have an effective echo delay time that corresponds to a fat-induced phase shift that is closest to a multiple of 2*pi;

unwrapping the phase of the complex data set to obtain an initial B0 map;

correcting for a global phase error and local phase errors present in the initial B0 map, thereby obtaining a phase-error corrected B0 map;

calculating a corrected fat-fraction map based on the phase-error corrected B0 map and a calculated bias frequency shift; and employing the corrected fat-fraction map to perform bias removal on the phase-error corrected B0 map and generating a final B0 frequency map.

In another aspect, there is provided a method of mapping of the main magnetic field (B0) of a magnetic resonance scanner, the method comprising:

receiving multiple gradient echo image data;

generating a complex data set based on selected echoes of the multiple gradient echo image data, wherein the selected echoes are selected to have an effective echo delay time that corresponds to a fat-induced phase shift that is closest to a multiple of 2*pi;

unwrapping the phase of the complex data set to obtain an initial B0 map;

correcting for a global phase error and local phase errors present in the initial B0 map, thereby obtaining a phase-error corrected B0 map; and performing bias removal on the phase-error corrected B0 map and generating a final B0 frequency map.

In another aspect, there is provided a method of mapping of the main magnetic field (B0) of a magnetic resonance scanner, the method comprising:

receiving multiple gradient echo image data;

generating a complex data set based on selected echoes of the multiple gradient echo image data, such that the complex data set is a pseudo-in-phase complex data set;

unwrapping the phase of the complex data set to obtain an initial B0 map;

correcting for a global phase error and local phase errors present in the initial B0 map, thereby obtaining a phase-error corrected B0 map; and performing bias removal on the phase-error corrected B0 map and generating a final B0 frequency map.

In another aspect, there is provided a magnetic resonance imaging system comprising:

a magnetic resonance scanner; and computing hardware operatively connected to said magnetic resonance scanner, said computing hardware comprising a processor coupled to a memory, wherein the processor, in response to executing instructions stored in the memory, is configured to:

process multiple gradient echo image data to generate a magnitude-based water mask;

generate a complex data set based on selected echoes of the multiple gradient echo image data, wherein the selected echoes are selected to have an effective echo delay time that corresponds to a fat-induced phase shift that is closest to a multiple of 2*pi;

unwrap the phase of the complex data set to obtain an initial B0 map;

calculate a bias frequency shift based on a calculated phase shift of fat during acquisition of the selected echoes and the effective echo time;

calculate a bias-corrected phase shift of fat that is produced during acquisition of the selected echoes;

employ the magnitude-based water mask to correct for a global phase error present in the initial B0 map, thereby obtaining a globally phase-error-corrected B0 map;

employ the bias-corrected phase shift of fat to correct for local phase errors in the globally phase-error-corrected B0 map, thereby obtaining a phase-error corrected B0 map;

calculate a corrected fat-fraction map based on the phase-error corrected B0 map and the bias frequency shift; and employ the corrected fat-fraction map to perform bias removal on the phase-error corrected B0 map and generating a final B0 frequency map.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

(D) error-corrected B0 map from the same channel as (A); (E) the channel-combined B0 map; (F) and (G) are the final channel-combined water-only and fat-only images, respectively.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Figure 1:
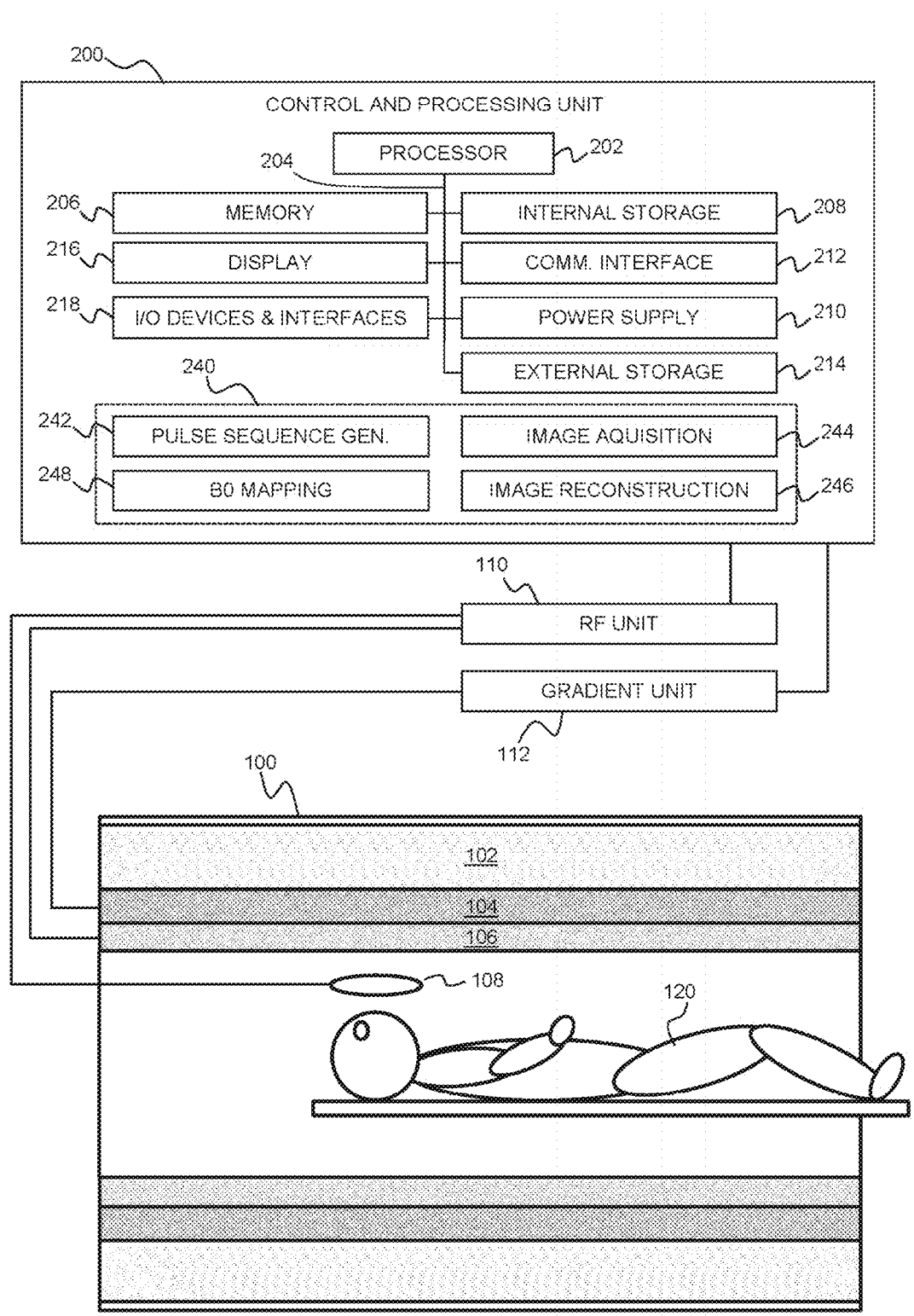
FIG. 1 is a block diagram of an example system for performing various methods of the present disclosure.

Referring now to FIG. 1, an example magnetic resonance (MR) system is provided for performing methods disclosed herein. The example system includes a magnetic resonance scanner 100 that employs a main magnet 102 to produce a main magnetic field B0, which generates a polarization in a patient 120 or the examined subject. The example system includes gradient coils 104 for generating magnetic field gradients. A reception coil 108 detects the MR signals from patient 120. The reception coil 108 can also be used as a transmission coil. Alternatively, body coil 106 may be employed to radiate and/or detect radio frequency (RF) pulses. The RF pulses are generated by an RF unit 110, and the magnetic field gradients are generated by a gradient unit 112. The manner by which MR signals are detected using the sequence of RF pulses and magnetic field gradients, and how MR images are reconstructed in general, are known to those skilled in the art.

It will be understood that the MR system can have additional units or components that are not shown for clarity, such as, but not limited to, additional control or input devices, and additional sensing devices, such as devices for cardiac and/or respiratory gating. Furthermore, the various units can be realized other than in the depicted separation of the individual units. It is possible that the different components are assembled into units or that different units are combined with one another. Various units (depicted as functional units) can be designed as hardware, software or a combination of hardware and software.

Control and processing unit 200 obtains magnetic resonance images of patient 120 according to a gradient echo pulse sequence, as described in further detail below. Control and processing unit 200 is interfaced with magnetic resonance imaging scanner 100 for receiving acquired images and for controlling the acquisition of images. Control and processing unit 200 receives image data from RF unit 110 and processes the imaging data according to the methods described below.

FIG. 1 provides an example implementation of control and processing unit 200, which includes one or more processors 202 (for example, a CPU/microprocessor), bus 204, memory 206, which may include random access memory (RAM) and/or read only memory (ROM), one or more optional internal storage devices 208 (e.g. a hard disk drive, compact disk drive or internal flash memory), a power supply 210, one more optional communications interfaces 212, optional external storage 214, a display 216, and one or more input/output devices and/or interfaces 218 (e.g., a receiver, a transmitter, a speaker, a display, a user input device, such as a keyboard, a keypad, a mouse, a position tracked stylus, a position tracked probe, a foot switch, and/or a microphone for capturing speech commands). Control and processing unit 200 may include many more or less components than those shown.

Although only one of each component is illustrated in FIG. 1, any number of each component can be included in control and processing unit 200. For example, a computer typically contains a number of different data storage media. Furthermore, although bus 204 is depicted as a single connection between all of the components, it will be appreciated that the bus 204 may represent one or more circuits, devices or communication channels which link two or more of the components. For example, in many computers, bus 204 often includes or is a motherboard.

In one embodiment, control and processing unit 200 may be, or include, a computer or any other hardware equivalents. Control and processing unit 200 may also be implemented as one or more physical devices that are coupled to processor 202 through one of more communications channels or interfaces. For example, one or more components of control and processing unit 200 can be implemented using application specific integrated circuits (ASIC). Alternatively, control and processing unit 200 can be implemented as a combination of hardware and software, where the software is loaded into the processor from the memory or over a network connection.

Control and processing unit 200 may be programmed with a set of instructions which when executed in the processor causes the system to perform one or more methods described in the disclosure. For example, as shown in FIG. 1, control and processing unit 200 may be programmed with instructions in the form of a set of executable modules 240 (the executable instructions may be stored in memory 206), such as, but not limited to, pulse sequence generation module 242, image acquisition module 244, image reconstruction module 246, and B0 mapping module 248.

Modules 242, 244 and 246 may be implemented using algorithms known to those skilled in the art for pulse sequence generation, image acquisition, and image reconstruction, respectively. Pulse generation module 242 establishes the sequence of RF pulses and magnetic field gradients depending on the desired imaging sequence, and image acquisition module 244 that stores the MR signals detected by the coils 108 and/or 106 in raw data space. Image reconstruction module 246 processes the acquired image data to perform image reconstruction of an MR image. According to various aspects of the present disclosure, a B0 mapping module is provided for processing image data and generating a corrected B0 map. The corrected B0 map be employed by image reconstruction module 246. While the control and processing system of FIG. 1 is shown as implementing the B0 mapping algorithm in the present example implementation, it will be understood that the methods of the present disclosure need not be performed on a computing device that is directly or indirectly connected to the magnetic resonance scanner, and that the methods of the present disclosure, or portions of the methods of the present disclosure, may be performed on a separate and disconnected computing system to post-process the image data, Some aspects of the present disclosure can be embodied, at least in part, in software. That is, some methods can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASICs), or firmware such as electrically erasable programmable read-only memory (EEPROMs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. As used herein, the phrases "computer readable material" and "computer readable storage medium" refers to all computer-readable media, except for a transitory propagating signal per se. Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others.

As noted above, various embodiments of the present disclosure provide systems and methods for the generation of a corrected B0 map, and for the generation of images, and/or other measures of interest, based on a corrected B0 map, and based on the processing of multi-echo gradient echo data.

Figure 2A:
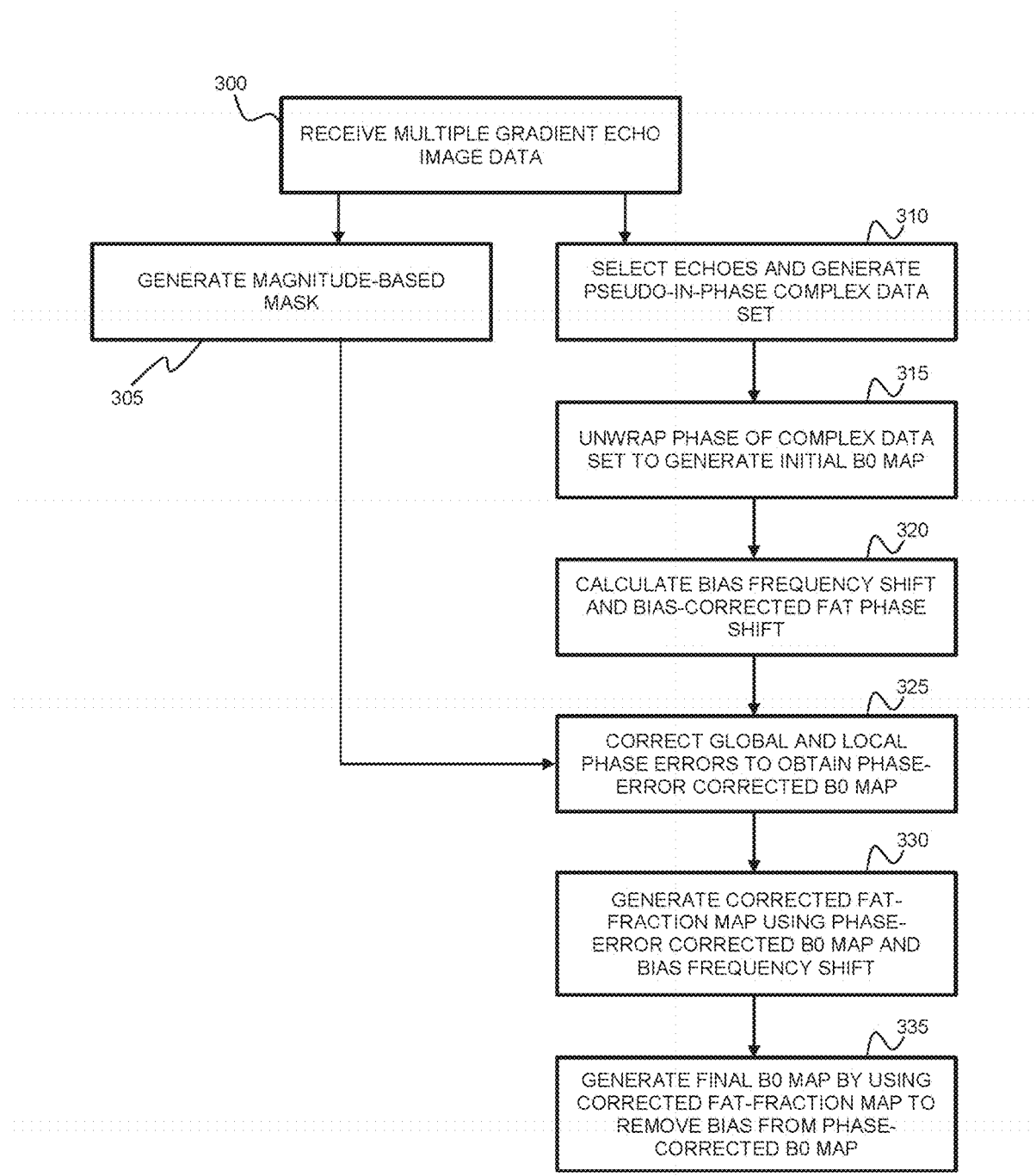
FIG. 2A is a flowchart illustrating a method of performing B0 mapping according to an example embodiment of the present disclosure.

Referring now to FIG. 2A, a flow chart is shown that illustrates an example method of performing B0 mapping according to the present disclosure. As shown at 300, multi-echo gradient echo image data is received. For example, an MR scanning system may be employed to collect MR image data from a subject using a multi-echo pulse sequence known to those skilled in the art. Non-limiting examples of such sequences include IDEAL/IDEAL-IQ on a GE scanner, mDIXON on a Philips scanner and MEGE on a Siemens scanner.

As shown at 310, a complex data set is generated based on the multi-echo image data. The complex data set is generated from the multi-echo image data by selecting echoes such that fat signals associated with the selected echoes are approximately in phase (pseudo-in-phase), such that the unwrapping of the phase complex data set is suitable for generating an initial B0 phase map ($\varphi_{b0,ini}$). In some embodiments, the complex data set is obtained by calculating a Hermitian product ("synthetic Hermitian multiplication") of the signals from the selected echoes. An effective echo time ($\Delta TE_{b0}$) can then be derived from the known echo times and subsequently used to define a scaling factor ($1/2\pi\Delta TE_{b0}$) for converting phase to frequency. This scaling factor may be employed, for example, for converting a B0 phase map into a B0 frequency map.

Various example methods of selecting appropriate echoes for generating the complex data set, henceforth referred to as $S_{b0}$, are now described. The selection of the echoes for calculating $S_{b0}$ is based on the determination of a suitable or optimal $\Delta TE_{b0}$, which is the $\Delta TE$ closest to the time period required for fat to experience a phase shift of $2\pi$ (or multiples of $2\pi$). Different echo-selection strategies are implemented in according to the example methods presented herein, in order to accommodate acquisitions with both uniformly and non-uniformly spaced echoes. It will be shown that both strategies may be based on estimating the values of the relative phase difference between fat and water for different echoes.

The phase difference can be estimated as follows. When B0 off-resonance is present in raw multi-echo data, the signal (S) from a pixel or voxel (it is noted that the terms voxel and pixel are used interchangeably in the present disclosure, where a pixel pertains to a spatial location within a two-dimensional slice, and a voxel refers to a spatial location within a three-dimensional volume) containing water and fat at the $j^{th}$ echo can be written, using a multi-peak fat model, as follows (5):

$$S=(\rho_W+\rho_F\Sigma_{m=1}^{M}a_m e^{i2\pi\Delta f_m TE_j})e^{i2\pi f_{b0}TE_j}e^{-R2^*Te_j}, \quad [1]$$

where $\rho_W$ and $\rho_F$ are the signals of the water and fat components, respectively; $a_m$ is the known relative intensity of the $m^{th}$ peak of the fat spectrum, $\Delta f_m$ is the corresponding relative frequency shift from water, and M is the total number of peaks of the multi-peak fat model.

Neglecting the unknown phase terms in $\rho_W$ and $\rho_F$, Eq. 1 can be rewritten into a magnitude term ($S_{mag}$) and a phase term ($\varphi$), as follows:

$$S_{mag}(FF,TE_j,R_2^*)=(|\rho_W|+|\rho_F|)(1-FF)+FF \\ (\Sigma_{m=1}^{M}a_m e^{i2\pi\Delta f_m TE_j})|e^{-R2^*TE_j} \quad [2a]$$

$$\varphi(FF,TE_j,f_{b0})=\mathrm{wrap}(\varphi_{fw,j}(FF,TE_j)+2\pi f_{b0}TE_j), \quad [2b]$$

where the fat-fraction FF is defined as $|\rho_F|/(|\rho_W|+|\rho_F|)$; and where "wrap" is an operator that constrains phase values to the range of $[-\pi\pi)$. Given this expression for the fat-fraction, the phase term ($\varphi_{fw}$) related to the chemical shift is then:

$$\varphi_{fw,j}(FF,TE_j)=\mathrm{angle}((1-FF)+FF\Sigma_{m=1}^{M}a_m e^{i2\pi\Delta f_m TE_j}). \quad [2c]$$

The phase difference among different echoes due to the presence of fat, $\Delta\varphi_{fw,ini}$, can thus be calculated or estimated based on Eq. 2c, where FF=1. It will be understood that equation 2c may be employed as modeling one or more fat peaks. For example, in some embodiments, a 6-peak fat model (19) may be employed.

Figure 3:
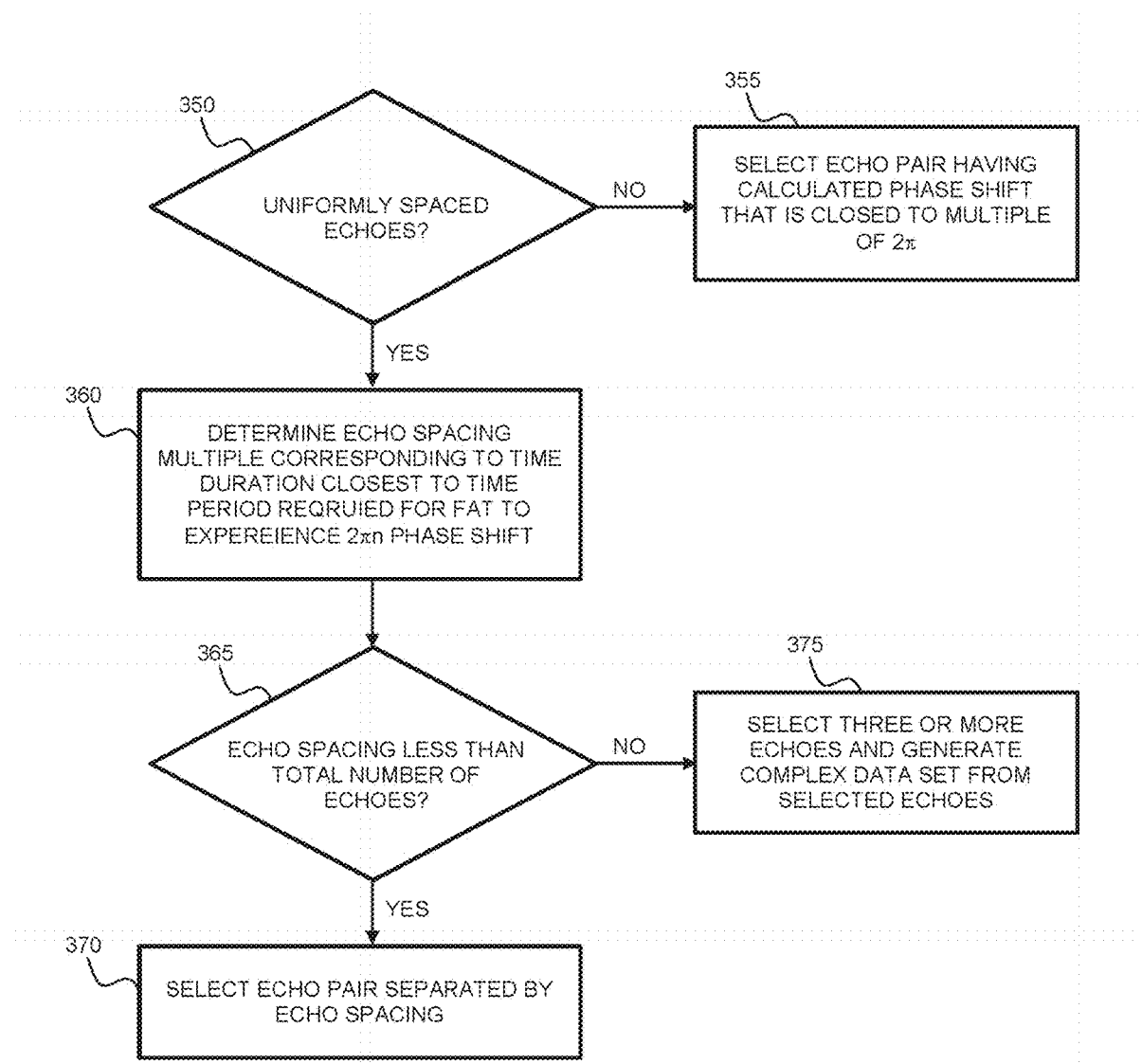
FIG. 3 is a flowchart illustrating an example method of echo selection for the generation of a pseudo-in-phase complex data set.

A specific example implementation for the selection of suitable echoes for the generation of the complex data set is illustrated in the flow chart shown in FIG. 3. For datasets acquired with uniformly spaced echoes, as shown at 350 and 360, $\Delta TE_{b0}$ is always equal to a multiple of the echo spacing $\Delta TE$, i.e. $\Delta TE_{b0} = I_{b0} \Delta TE$, where $I_{b0}$ is an integer. Thus, optimizing $\Delta TE_{b0}$ through echo-selection equates to estimating an optimal value of $I_{b0}$. With the single-peak fat model, the optimal $I_{b0}$ value is equal to round($2\pi/|wrap(2\pi f_{CS} \Delta TE)|$) with $\Delta TE \neq 1/f_{CS}$. Similarly, with the multi-peak model, the optimal $I_{b0}$ value is estimated by round($2\pi/(\sum_{j=1}^{N_e-1} |wrap(\varphi_{fw,j+1} - \varphi_{fw,j})|/(N_e-1))$), where $N_e$ denotes the total number of echoes. The echoes for generating $S_{b0}$ are then identified given the knowledge of the optimal $I_{b0}$ and the known $N_e$.

As shown in FIG. 3 at 370, if $I_{b0}$ is less than $N_e$ for image data based on evenly spaced echoes, two echoes with an index difference equal to $I_{b0}$ are selected. On the other hand, as shown at 375, if $I_{b0}$ is equal to or larger than $N_e$, selecting more than two echoes and designing a specific formula for $S_{b0}$ may be needed.

For example, when both the optimal $I_{b0}$ and $N_e$ are equal to three, one can generate $S_{b0}$ from all three echoes using the formula $((S_3 S_2)(S_3 S_1))$; in this case $DTE_{b0}$ is equal to $(2TE_3 - TE_2 - TE_1)$ (i.e. 3D TE). Practically, when an operator prescribes scanning parameters, the TEs are known or have been pre-selected to the optimized values. Therefore, selecting appropriate echo times and building a formula for constructing the complex data set for calculating B0 can be achieved automatically. For example, in the case of $N_e=4$, $I_{b0}=5$, one can use $(S_4 S^*_1)(S_3 S^*_1)$. Typically, when a sequence with more than three TEs is implemented on a scanner or used with a preset protocol, a pair of echoes is usually already suitable for B0 mapping.

As shown at 355 in FIG. 3, in order to select suitable echoes from a dataset acquired with non-uniformly spaced echoes, values of $\Delta \varphi_{fw,ini}$ are calculated over all possible echo-pairs, and the paired echoes with $\Delta \varphi_{fw,ini}$ less than a pre-selected (e.g. user-defined) threshold value relative to a multiple of an (for example, ±0.1π) are identified. In one example implementation, if only a single pair is identified, the two echoes included in this pair are selected; while if multiple paired echoes are identified, the pair with the minimum TE difference and the shortest TE value among all identified pairs, is selected, because high SNR in $S_{b0}$ is desired.

Referring again to 310 of FIG. 2A, once the echoes are selected, the complex data set, $S_{b0}$ is generated, as described above. It is noted that the selection of suitable echoes results in a complex data set based on fat signals that are "pseudo-in-phase".

After having generated the complex data set, the phase of the complex data set it is unwrapped, as shown at 315 in FIG. 2A, using a suitable phase unwrapping method. It will be understood that there are many different phase unwrapping methods that are known in the art, and which may be employed to perform the phase unwrapping step. A non-limiting example of a suitable phase unwrapping method is the PUROR unwrapping algorithm (20). The phase unwrapping step results in an initial B0 map, which may be generated in the form of a phase map, frequency map, or any other suitable method map form.

The unwrapped phase term of $S_{b0}$ corresponds to the phase difference between the echoes and is the sum of phase-shifts caused by different sources:

$$\varphi_{b0,ini} = \varphi_{b0} + \varphi_{un}^{error} + \varphi_{fw,ini}, \qquad [3]$$

where $\varphi_{b0}$ is caused by B0 inhomogeneity; $\varphi_{un}^{error}$ represents the unwrapping phase error (unknown multiple of $2\pi$ phase shifts); and $\varphi_{fw,ini}$ is a bias term related to the chemical-shift between fat and water and is dependent on $\Delta TE_{b0}$. The challenge is to remove the two error terms ($\varphi_{un}^{error}$ and $\varphi_{fw,ini}$).

The first challenge in obtaining an accurate B0 map is to remove $\varphi_{un}^{error}$. Unwrapping errors can affect the initial B0 map globally or locally. Global phase unwrapping errors arise because phase values in the unwrapped image are relative, i.e. the entire initial B0 phase map may be shifted by a multiple of $2\pi$ (we define the term $\varphi_g^{un}$, the subscript g indicating a global effect). Second, local phase errors ($\varphi_l^{un}$, the subscript/referring to a local effect) may exist in regions where larger-than-π phase gradients exist in the real B0 map. It is important to note that for all phase unwrapping methods—which incorporate a constraint that the spatial phase gradient is less than π—the performance of phase unwrapping is sensitive to noise, large jumps at the interface between tissue and air, large B0 inhomogeneity, and singularities.

The presented example method identifies and corrects both global and local phase errors, as shown at step 325 in FIG. 2A, by evaluating a B0-corrected phase image of the Hermitian-product between the $j^{th}$ and $(j+1)^{th}$ echoes ($\Delta \varphi_{j,j+1}^{ori}$). The B0-corrected phase ($\Delta \varphi^{corr}$) is given by:

$$\Delta \varphi^{corr} = \Delta \varphi_{j,j+1}^{ori} - \varphi_{b0,ini} \Delta TE_{j,j+1} / \Delta TE_{b0} \qquad [4a]$$

$$= (\Delta \varphi_{j,j+1}^{ori} - 2\pi \times f_{b0} \Delta TE_{j,j+1}) + \varphi_{un}^{error} \qquad [4b]$$

where $\Delta TE_{j,j+1}$ is the difference of TEs between two consecutive echoes $(TE_{j+1} - TE_j)$; $\varphi_{un}^{error}$ includes two terms caused by $\varphi_g^{un}$ and $\varphi_l^{un}$:

$$\varphi_{un}^{error} = -(\varphi_g^{un} + \varphi_l^{un}) \Delta TE_{j,j+1} / \Delta TE_{b0}. \qquad [4c]$$

The evaluation process is based on the following observations: if no phase error is present in the initial B0 map all water-only pixels have near zero phase values ($\Delta \varphi^{corr} \approx 0$); the fat-only pixels have phase values close to a phase term ($\Delta \varphi^{fat}$) approximated using Eq. 2c with FF=1; the other pixels have phase values between 0 and $\Delta \varphi^{fat}$. These observations lead to a first criterion for guiding phase-error correction: the values of $\Delta \varphi^{corr}$ of all tissue-pixels should be in the range between zero and $\Delta \varphi^{fat}$.

However, the first criterion is not sufficient to differentiate fat/water swaps, especially when the images or regions are predominantly occupied by water or fat. To solve this ambiguity, the present example method generates two separate water masks—a phase based water mask from a thresholded $\Delta \varphi^{corr}$ and a magnitude-based water mask from a thresholded magnitude-based FF map—and imposes a second criterion that the two masks must match. The magnitude-based water mask is generated as shown in step 305 of FIG. 2A, and is subsequently employed in global phase error correction, as shown at step 325.

The magnitude-based water mask can be generated according to a number of different methods. In one example, in which three or more echoes are detected, the following method may be employed, as illustrated in the flow chat shown in FIG. 4. Theoretically, to achieve full-range FF mapping (0-100%) only based on magnitude information a multi-peak fat model must be used. Prior to applying pixel-by-pixel magnitude fitting using Eq. 2a, it was demonstrated that fat pixels fall along a non-exponential curve, while the water curve follows the expected exponential decay.

Figure 4:
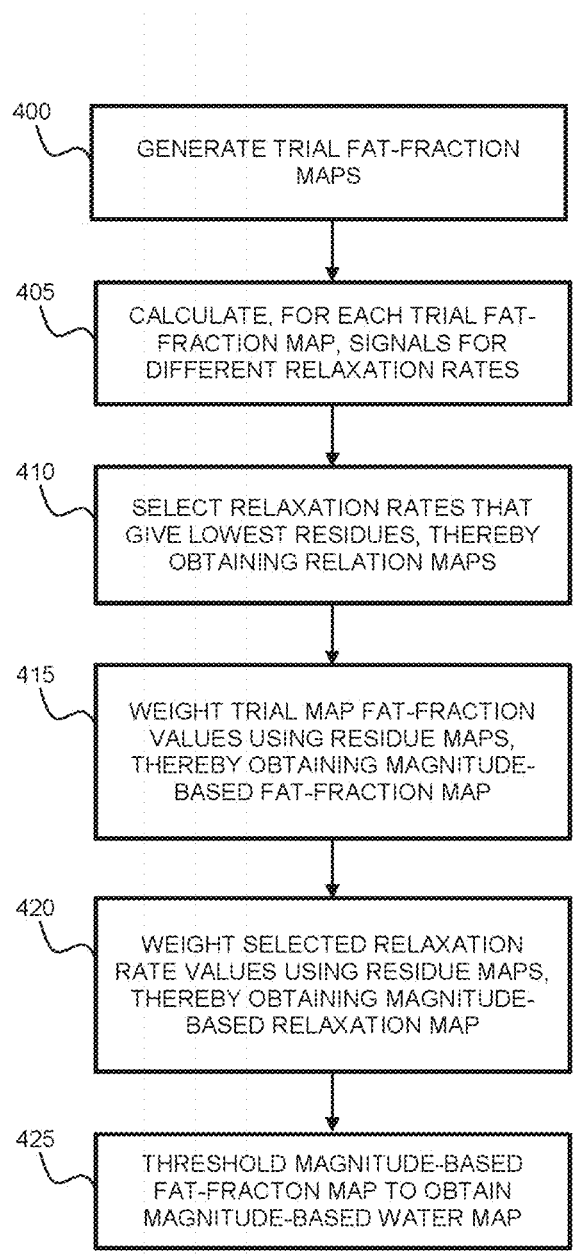
FIG. 4 is a flowchart illustrating an example method of generating a magnitude-based water map.

The first step in the present example magnitude fitting method shown in FIG. 4 involves normalization of the $(|\rho_W|+|\rho_F|)$ term in Eq. 2a over all echoes by using the magnitude value from the first echo; correspondingly $TE_1$ is subtracted from the TEs of all echoes. To estimate the two remaining unknown variables (FF and R2*) in Eq. 2a, a set of trial fat-fraction maps are generated by setting the fat-fraction of all voxels equal to a set of discrete values between 0 and 1 ($FF_t$, t denotes the trial value), as shown at 400 in FIG. 4. For each $FF_t$, a residue map is also calculated by varying the R2* value and comparing against the measured magnitude—the R2* yielding the lowest residue ($RES_t$) for a given pixel is used to generate the trial R2* map ($R_{2,t}^*$), as shown at 405 and 410. By repeating the above procedure several times with different FF values, an R2* map and a magnitude-based FF map can be obtained by calculating the weighted average of the R2* and FF used in each $FF_t$ iteration above, as shown at 415 and 420:

$$R_2^* = (\Sigma_{t=1}^T w_t R_{2,t}^*)/(\Sigma_{t=1}^T w_t), \quad [5a]$$

and $$FF_{mag} = (\Sigma_{t=1}^T w_t FF_t)/(\Sigma_{t=1}^T w_t), \quad [5b]$$

where T is the total number of the tested FF values and the weighting factor $w_t = 1/RES_t$.

From the magnitude-based FF map, a threshold value (e.g. a pre-selected threshold, such as a user-specified threshold) can be used to generate a binary magnitude-based water mask, as shown at 425, for use in verifying the phase errors in the aforementioned global phase error correction method (i.e. in step 325 of FIG. 2A. It is noted that the R2* map generated from Eq. 5a can be used as the final R2* map.

In one example implementation, the range of FF values is set from 0 to 1.0, for example, in steps of 0.1; the range of R2* is set, for example, from 0 to 300 s$^{-1}$ with an interval of 5 s$^{-1}$; pixels with a magnitude-based FF less than 0.3 are included in the magnitude-based water-mask. It is noted that the aforementioned range of R2* values is prescribed to pertain to tissue properties, which are commonly falling in this range. The interval of 5 s$^{-1}$ is selected for considering both accuracy and computational cost: a smaller value is better but will increase computational time, and the same trade off pertains to the selection of the values for the FF mask.

In the preceding embodiment, unipolar multi-echo (total echo number>2) GRE data are acquired and magnitude-based masks are generated through pixel-by-pixel fitting. Alternatively, the various embodiments of the present disclosure can be adapted to process a conventional dual-echo GRE data set. More particularly, because pixel-by-pixel fitting cannot be performed for dual-echo acquisitions, the magnitude-based masks can be generated based on the difference of signal intensity or texture features between fat and water based on the difference of signal intensity or texture features between fat and water.

Figure 2B:
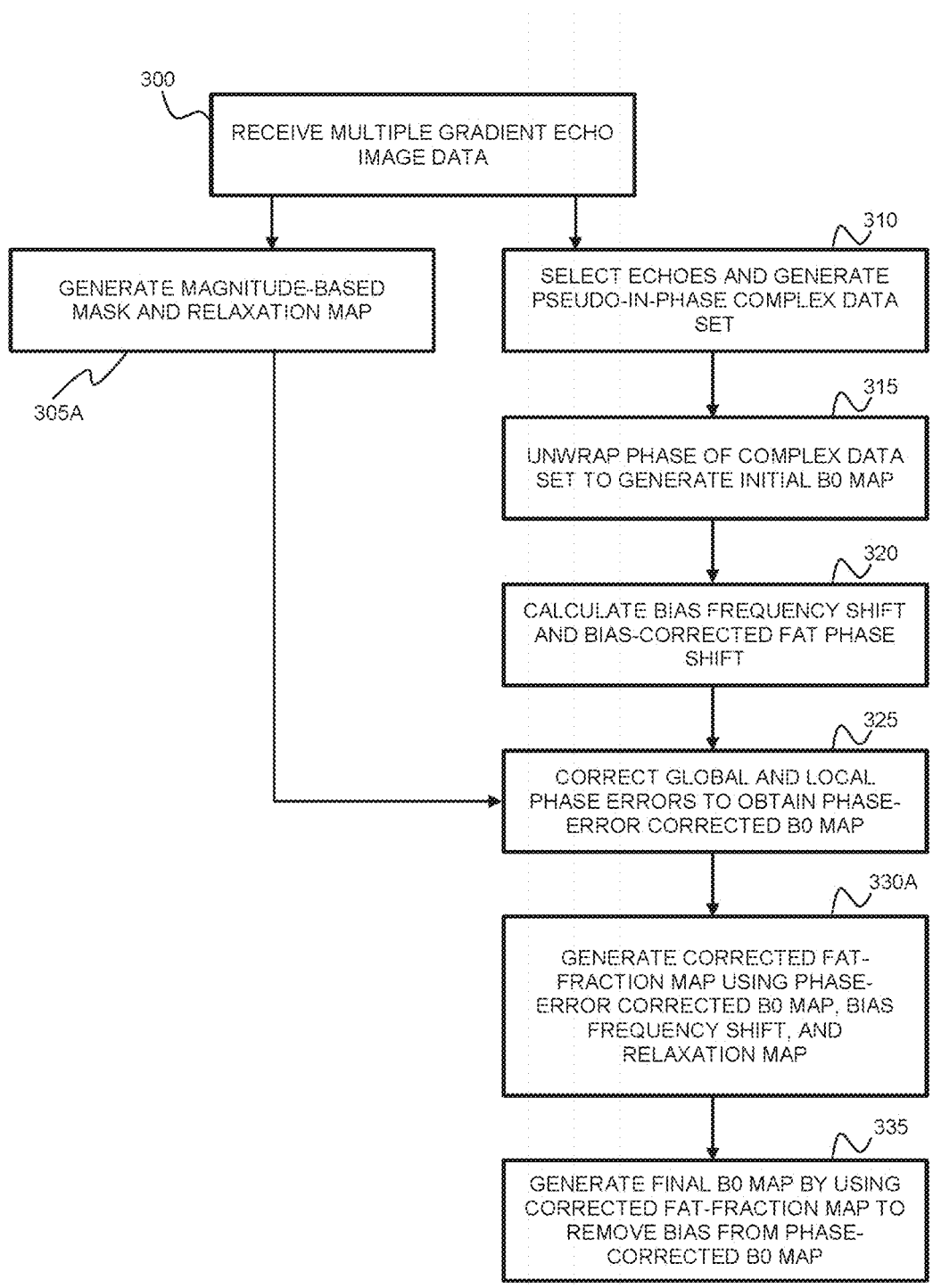
FIG. 2B is a flowchart illustrating a method of performing B0 mapping according to another example embodiment of the present disclosure.
Figure 5:
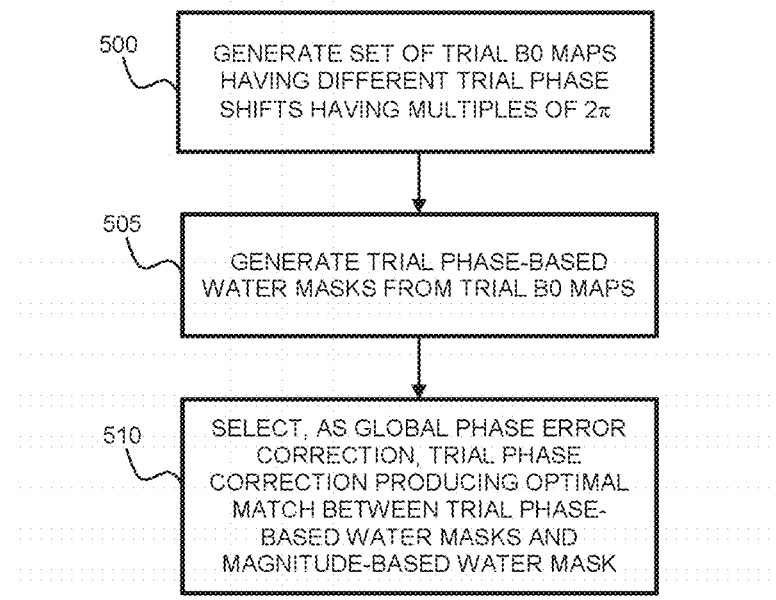
FIG. 5 is a flowchart illustrating an example method of performing global phase error correction.

The magnitude-based water map, which may be generated as described above, is then employed for global phase error correction in step 325 of FIGS. 2A and 2B. An example method of global phase-error correction is illustrated in the flow chart shown in FIG. 5. In this present example method, both the global and local phase error corrections are performed sequentially, on a slice-by-slice basis. To determine the unknown global phase shift, a set of B0 map templates is generated by shifting the initial B0 phase map with a set of multiples of $2\pi$, as shown at 500 in FIG. 5:

$$\varphi_{b0,ini}^{shift} = \varphi_{b0,ini} + 2\pi n_{g,t}, \quad [6]$$

where $n_{g,t}$ is an integer in the range of $\pm(\text{round}(\Delta TE_{b0}/\Delta TE)-1)$. Each trial B0 map is used to perform background removal using Eq. 4a. The pixels with phase values of $\Delta\varphi^{corr}$ less than $0.1\pi$ are included in a phase-based water mask, as shown at 505.

For each trial B0 map, the matched ratio between the corresponding trial phase-based water mask and the magnitude-based water mask is calculated as the total number of pixels identified by both water masks divided by the total number of pixels included in the magnitude-based mask. Among these trials, the one with the highest match ratio is considered as the correct one, as illustrated at 510 in FIG. 5. In the case where the same match ratio is obtained from two different values of $n_{g,t}$, separated by round($\Delta TE_{b0}/\Delta TE$), the one with the smaller absolute value of $n_g$ is selected. Once the value of $n_g$ is determined, the initial B0 phase map is shifted by $2\pi n_g$, resulting in a $\varphi_g^{un}$-corrected B0 map.

After performing global phase-error correction, local phase-error correction is performed on the globally phase-error corrected B0 map. However, prior to performing this step, a bias-corrected value for the fat phase shift ($\Delta\varphi^{fat}$) that accrues during acquisition is first calculated, as shown at 320 in FIG. 2A.

Figure 6A:
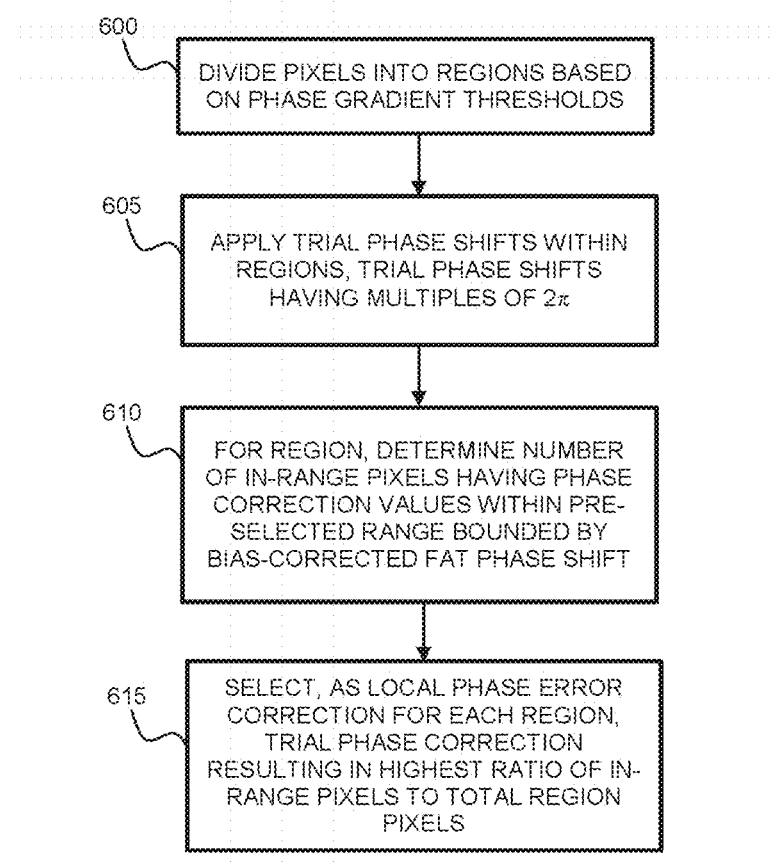
FIG. 6A is a flowchart illustrating an example method of performing local phase error corrections.
Figure 6B:
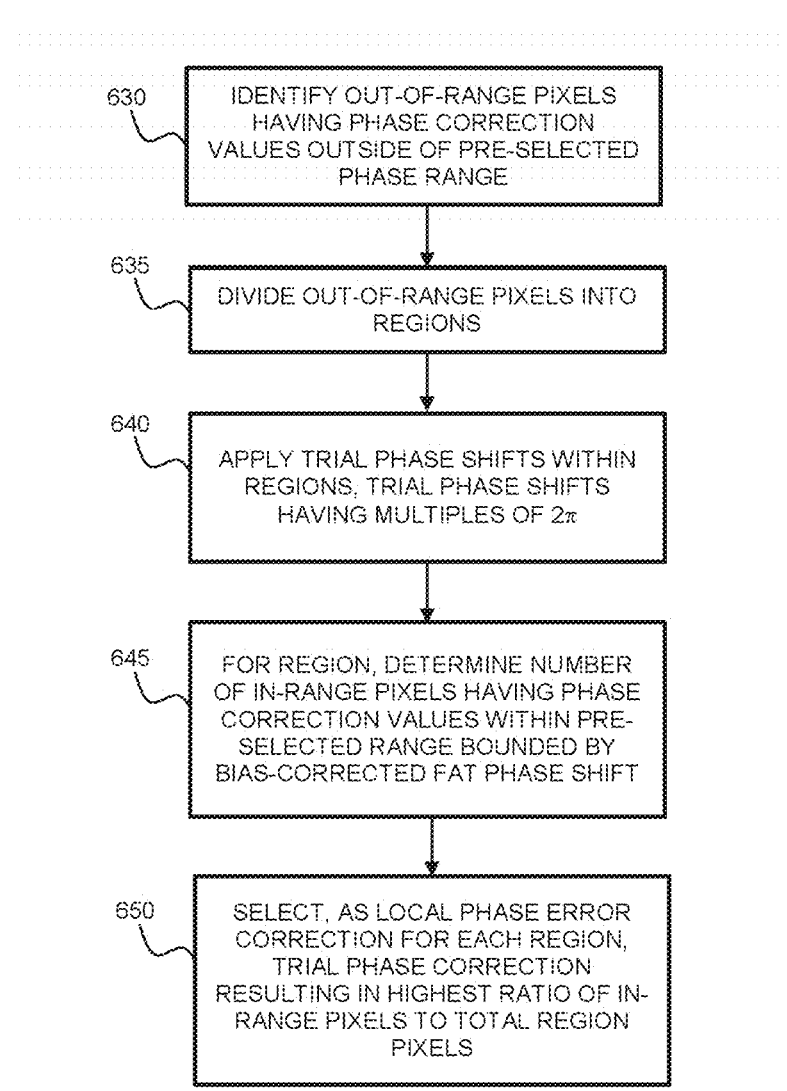
FIG. 6B is a flowchart illustrating an example method of performing additional local phase error corrections.
Figure 6C:
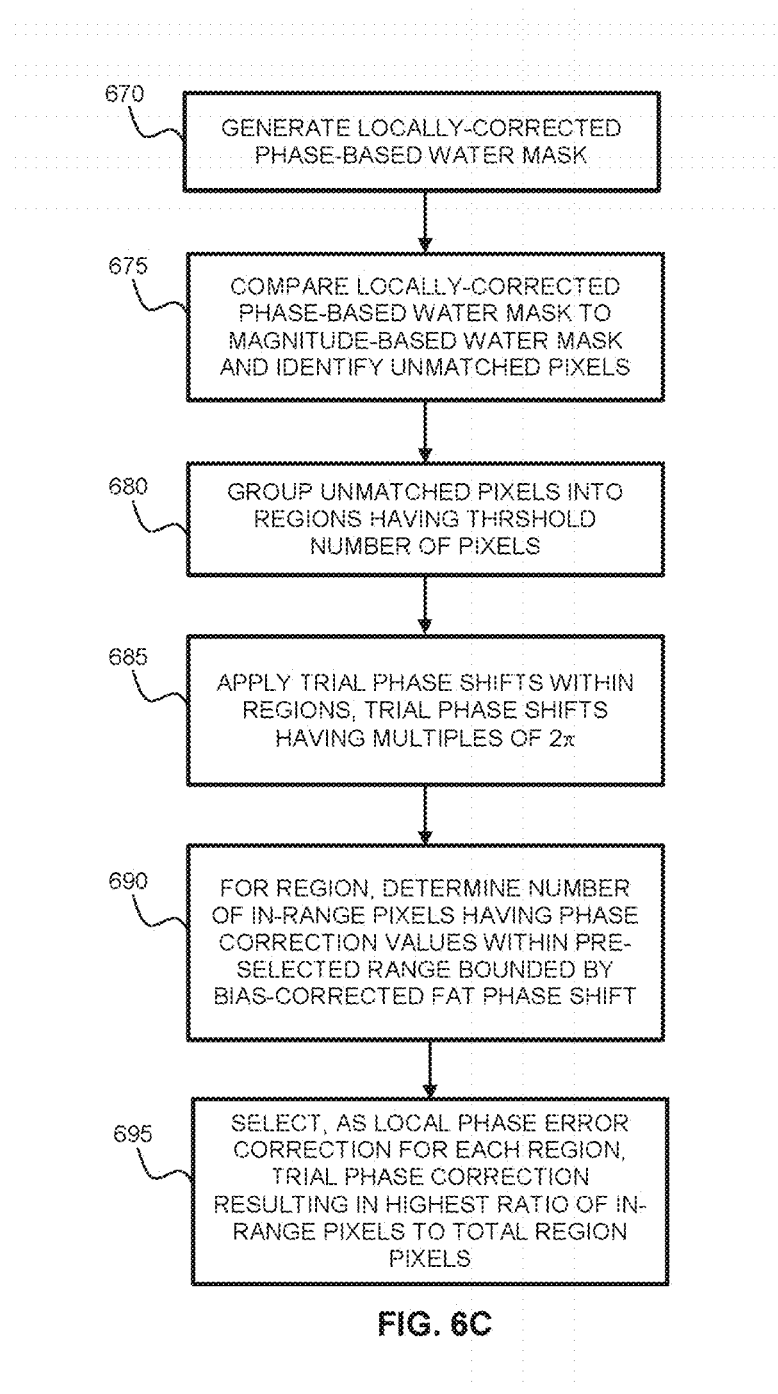
FIG. 6C is a flowchart illustrating another example method of performing additional local phase error corrections.

The process of local phase-error correction may be performed as illustrated in the flow charts shown in FIGS. 6A-C. As illustrated at 600 in FIG. 6A, pre-selected (e.g. user-specified) thresholds of the phase gradient ($\pi$) are used to divide the $\varphi_g^{un}$-corrected B0 map into regions. For each region, the total number of pixels that have phase values of $\Delta\varphi^{corr}$ (calculated as described above) in the range of $[-0.25\times\Delta\varphi^{fat} \Delta\varphi^{fat}]$ and $[\Delta\varphi^{fat} -0.25\times\Delta\varphi^{fat}]$ for positive and negative $\Delta\varphi^{fat}$, respectively, are determined; and an "in-range ratio" is calculated as the total number of pixels that fall in the above range divided by the total number of pixels, as shown at 610.

The value for $\Delta\varphi^{fat}$ is calculated as follows. Eq. 2c is employed, with FF=1, to calculate the phase shift $\Delta\varphi_{fw,ini}$ between echoes due to the chemical shift due to fat. Using the values of $\Delta\varphi_{fw,ini}$ and $\Delta TE_{b0}$, the $\varphi_{fw}$ value is the re-calculated using the bias-corrected fat model in order to obtain the value of $\Delta\varphi^{fat}$. This can be achieved by calculating $f_{bias} = \Delta\varphi_{fw,ini}/(2\pi\Delta TE_{b0})$ then replacing the original chemical shift with the bias-corrected values (i.e. $\Delta f_{m,bias} = \Delta f_m - f_{bias}$).

The in-range ratio is calculated for each trial B0 map with $n_{l,t}$—an integer in the range of $\pm(\text{round}(\Delta TE_{b0}/\Delta TE)-1)$. To satisfy the first criterion, the $n_{l,t}$ that results in the highest in-range ratio is selected and used to shift the phase values of the region by $2\pi n_l$, as shown at 615. It is noted that the process of identifying $n_l$ and $n_g$ is the same.

After having performed the local phase-error correction illustrated in FIG. 6A, further local phase-error corrections may be optionally determined. A first optional additional local phase-error correction method is illustrated in the example flow chart shown in FIG. 6B. In step 630, "out-of-range pixels" having phase correction values outside of the aforementioned range are identified. As shown at 635, the out-of-range pixels are then divided into regions (e.g. by identifying connected out-of-range pixels). The same strategy used in the FIG. 6A may then applied to determine the value of $n_l$, as shown at 640-650. It is noted that if two different values of $n_{l,t}$ result in the same in-range number, the one with the smaller absolute value may be selected for the example methods illustrated in FIGS. 6A and 6B.

FIG. 6O illustrates another optional local phase-error correction that may be applied. As shown at 670, the phase-based water mask is re-generated using the phase map that is locally corrected using the aforementioned methods. Any pixels that are identified by the phase-based water mask, but not the magnitude-based water mask, are considered "unmatched" pixels and are grouped into regions of connected pixels, as shown at 675 and 680. If the region size is smaller than a pre-selected threshold (e.g. a threshold of at least 100, 250, or 500 pixels) then no further processing is performed. For each larger region, as shown at 680-695, the value of $n_l$ is determined as described in FIGS. 6A and 6B, in order to shift the mean phase value of $\Delta\varphi^{corr}$ to be close to zero.

Following correction for the global and local phase errors, and having thereby obtained a phase-corrected B0 map, removal of the bias term ($\varphi_{fw,ini}$) must be performed in order to generate an accurate B0 map (as can be seen from eqn. 3). Removal of the $\varphi_{fw,ini}$ term can be achieved in the pulse-sequence design using the conventional Dixon-based B0 mapping approaches which rely on true in-phase $S_{b0}$ (i.e., $\varphi_{fw,ini}=0$). For the conventional Dixon-based techniques, both echo times and the formulas for calculating $S_{b0}$ are designed to ensure that for a single-peak fat/water chemical shift ($f_{cs}$) $2\pi f_{cs}\Delta TE_{b0}$ is equal to a multiple of $2\pi$. However, for a general multi-echo acquisition, the $\Delta_{fw,ini}=0$ condition is rarely met and a bias term is introduced in the initial B0 map—primarily affecting fat-dominant pixels and resulting in a biased FF map if the standard multi-peak fat model (19) is used.

Referring again to FIG. 2A, the bias correction is applied as follows. A corrected FF map is obtained first obtained, as shown at 330. To obtain a corrected FF map from the phase-error corrected B0 map, the fat model is modified by calculating $f_{bias}=\Delta\varphi_{fw,ini}/(2\pi\Delta TE_{b0})$ (as described above and employed in the calculation of $\Delta\varphi^{fat}$) and then replacing the original chemical shift with the bias-corrected values (i.e. $\Delta f_{m,bias}=\Delta f_m-f_{bias}$). The corrected FF map may thus be calculated, for example, using a Penrose-Moore pseudoinverse method (5), employing the phase corrected B0 map and the bias chemical shift. The final B0 may be expressed as a frequency map using $\Delta TE_{b0}$:

$$f_{b0} = \frac{\varphi_{b0}^{corr} - FF\Delta\varphi_{fw,ini}}{2\pi\Delta TE_{b0}}. \quad [7]$$

In embodiments in which the multi-echo data includes three or more echoes, and where and R2* map (or a T2* map) is obtained during the calculation of the magnitude-based water map (e.g. as shown in FIG. 4), then the relaxation map may also be used in the calculation of the corrected fat-fraction map. This example embodiment is illustrated in FIG. 2B, where the relaxation map is generated in 305A and employed for the calculation of the corrected fat-fraction in 330A. It is noted that for cases in which more than two echoes are acquired, it has been widely accepted that including the relaxation map will improve accuracy of the fat-fraction map, resulting in more accurate bias removal. However, the aforementioned method may alternatively be performed without including employing the relaxation map. It is further noted that when two echoes are acquired (dual echo), the relaxation effects are typically relatively small and negligible.

It will be understood that the aforementioned example methods may be implemented using image data that is collected using two echoes, or three or more echoes (the example magnitude method illustrated in FIG. 4 may be employed using three or more echoes). Furthermore, the fat model may include a single peak, or may be a more precise multi-peak model. Generally, it has been found that superior results are obtained when three or more echoes are used, and where a multi-peak fat model is employed.

In cases where image data is acquired with three or more echoes, iterative nonlinear data fitting algorithms with a multi-peak model can be adapted (10, 18). In general cases with two or more echoes, as noted above, the magnitude-based water mask can be estimated based on the difference of image intensity or texture features between water and fat.

In some example embodiments, the B0 mapping methods disclosed herein may be implemented using data acquired with bipolar excitation pulses. In such implementations, before performing the B0 mapping method, phase errors due to gradient delays should be removed. Specifically, zero and first-order phase corrections should be performed on an echo-by-echo basis.

As noted above, the B0 mapping methods disclosed herein may be employed for data acquired using single- or multi-channel RF receive coils. When MR signals are collected by a multi-channel RF coil, complex images are reconstructed on a channel-by-channel basis. The resulting channel-by-channel complex images can be combined into a channel-combined data set by using phase sensitive approaches. When the present B0 mapping methods are employed to process channel-combined data set, the aforementioned implementation can be directly used to generate the final B0 map.

When the B0-NICE method is applied to each individual channel data, the final B0 map is calculated as magnitude-weighted mean over all channels.

EXAMPLES

The following examples are presented to enable those skilled in the art to understand and to practice embodiments of the present disclosure. They should not be considered as a limitation on the scope of the disclosure, but merely as being illustrative and representative thereof. Throughout these examples, the aforementioned methods of B0 mapping are referred to as the "B0-NICE" method, where the acronym "NICE" denotes the Non-Iterative Correction of phase-Errors.

Figure 7A:
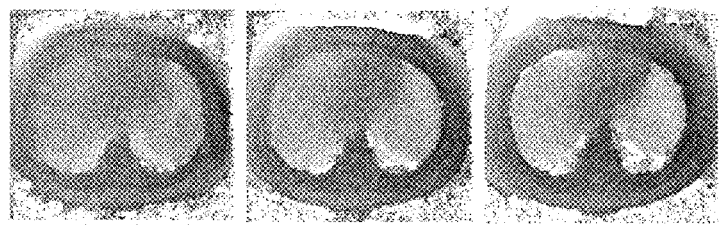
FIGS. 7A-C illustrates an example of processing a unipolar 6-echo GRE data set (IDEAL-IQ sequence) acquired using a GE 3.0 T scanner. (A) and (B) represent B0-NICE generated B0 maps and R2* maps for three consecutive slices (from left to right), respectively; (C) shows a comparison of FF maps between the IDEAL, IDEAL with B0-NICE, and B0-NICE for the three consecutive slices (from top to bottom), respectively. Fat/water swaps are observed in the FF map generated by using GE product software (indicated by arrows).
Figure 7B:
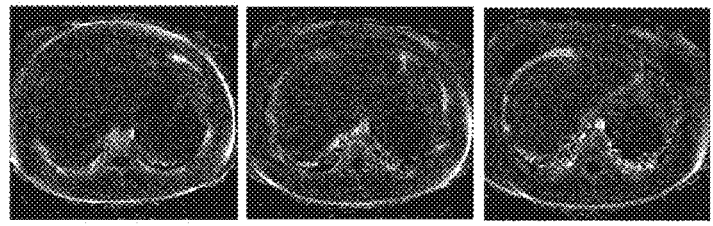
Figure 7C:
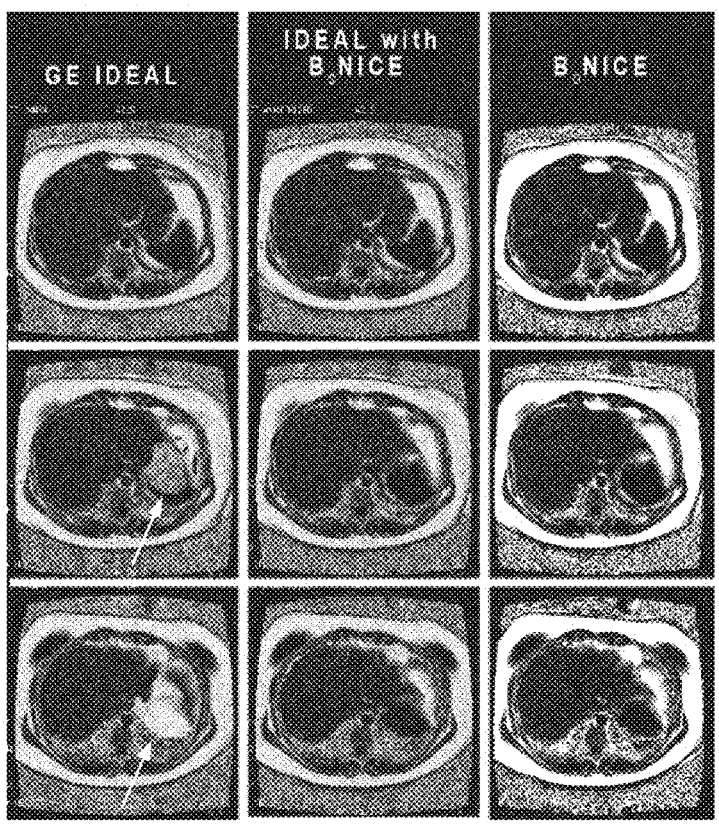

FIGS. 7A-C illustrate an example implementation based on imaging (unipolar 6-echoes, TE1/$\Delta$TE=1.2/1.0 ms) of a whole liver, which was processed as an example implementation of B0-NICE method illustrated in FIG. 2B. FIGS. 7A and 7B show the representative final B0 maps and R2* maps, respectively, of three consecutive slices. FIG. 7C shows the FF maps of the three slices obtained by using the GE IDEAL method, the IDEAL method modified according to the present B0-NICE method (in which the B0 map is generated using B0-NICE, then the B0 map is removed from the data set, resulting in a B0-corrected data set, and where The IDEAL technique is then applied to the B0-corrected data set), and the B0-NICE methods, from left to right, respectively. The results shown in FIG. 7C suggest the accuracy of B0 maps and demonstrate that B0-NICE method significantly improves the performance of IDEAL, where IDEAL introduces fat/water swaps. Note that channel-combination was conducted before applying the B0-NICE method.

Figure 8A:
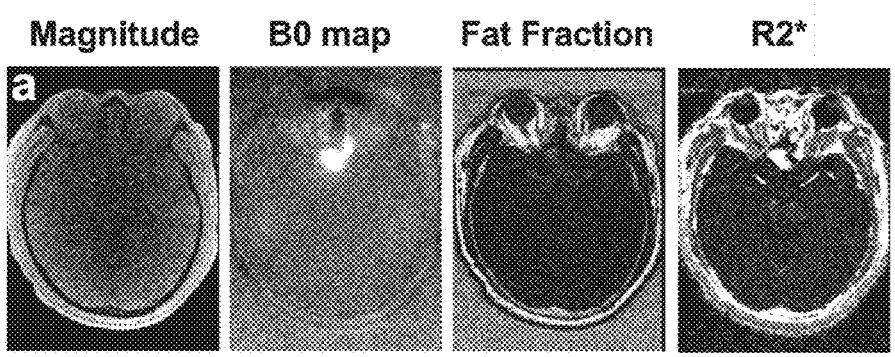
FIGS. 8A-C show an example of processing a bipolar 5-echo GRE data set acquired using a Siemens 3.0 T scanner: (A), (B) and (C) are the axial, coronal and sagittal orientation, respectively. From left to right are the magnitude image at the first echo, B0 map, Fat-fraction map and R2* map, respectively.
Figure 8B:
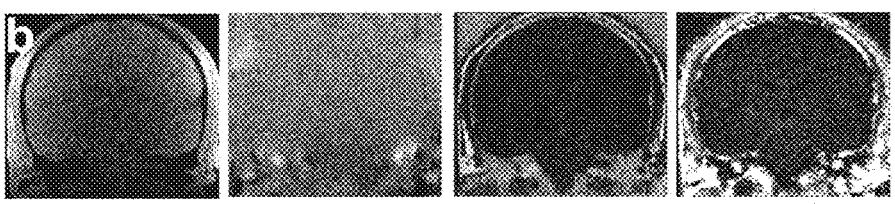
Figure 8C:

FIGS. 8A-C illustrate an example (bipolar 5-echoes, TE1/ΔTE=3.0/1.4 ms) of a whole head image acquisition, showing three different slices, respectively. As with the unipolar multi-echo acquisition, R2* map and magnitude-based FF map were generated from the magnitude only. However, an extra step has to be applied for bipolar acquisition in order to correct gradient-delay-related phase errors.

After the aforementioned step has been conducted, the B0-NICE method is applied to each individual channel data, followed by using magnitude-weighted channel combination. As demonstrated by FIGS. 8A-C, the B0-NICE implemented on a channel-by-channel basis works well for a 3D whole brain bipolar data set.

Figure 9A:
FIGS. 9A-G demonstrate an example of processing the bipolar dual-echo GRE data acquired using a Philips 1.5 T: (A) magnitude image from an individual channel; (B) phase image from the same channel as (A), where the bipolar-related phase error has been corrected; (C) initial B0 map from the same channel as (A), arrow pointing to phase error.
Figure 9B:
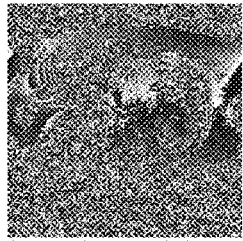
Figure 9C:
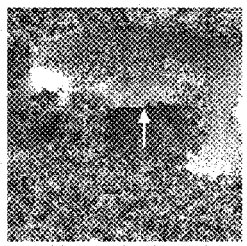
Figure 9D:
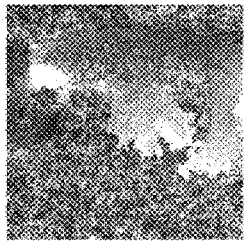
Figure 9E:
Figure 9F:
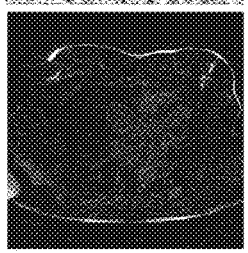
Figure 9G:
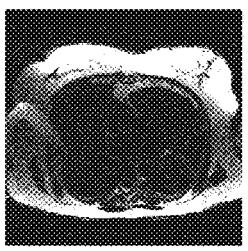

FIGS. 9A-G illustrate an example (bipolar 2-echoes, TE1/TE2=2.3/4.6 ms) of a whole-heart acquisition. Among Dixon techniques, the bipolar dual-echo technique is intrinsically the fastest, making it optimal for high resolution or 3D applications. To perform dual-echo fat-suppression, phase errors due to gradient delays should be removed; and if the removal is perfect, there should be no difference of conducting fat/water separation between bipolar and unipolar acquisition. To remove the unwanted B0 off-resonance effect, the convention dual-echo approach maps B0 simply using unwrapping but without phase error-correction, i.e., the outcome is determined by how well unwrapping performs. As shown in FIG. 9A, magnitude-based water- and fat-masks are generated, based on the fact that signal intensity from fat surrounding the chest wall is much higher than that from the heart for T1-weighted images. These masks are then used to correct phase errors (arrow in FIG. 9C) for generating phase error-corrected B0 maps (see FIG. 9D) for each channel, followed by combining them into final B0 maps (FIG. 9E) by using magnitude-weighted mean method. Note that the initial B0 map shown in FIG. 9O is obtained from FIG. 9B with phase unwrapping. Water-only and fat-only images are reconstructed using the two-point Dixon approach on a channel-by-channel basis. Final channel combination of water-only and fat-only images (FIGS. 5F and 5G) is performed using the sum of squares approach. This example demonstrates that extending B0-NICE to dual echo acquisition will improve the robustness of B0 mapping and fat-suppression using phase unwrapping.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

1. Reeder S B, Pineda A R, Wen Z, Shimakawa A, Yu H, Brittain J H, Gold G E, Beaulieu C H, Pelc N J. Iterative decomposition of water and fat with echo asymmetry and least-squares estimation (IDEAL): application with fast spin-echo imaging. Magn Reson Med 2005; 54(3):636-644.
2. Glover G H, Schneider E. Three-point Dixon technique for true water/fat decomposition with B0 inhomogeneity correction. Magn Reson Med 1991; 18(2):371-383.
3. Szumowski J, Coshow W R, Li F, Quinn S F. Phase unwrapping in the three-point Dixon method for fat suppression M R imaging. Radiology 1994; 192(2):555-561.
4. Hernando D, Kellman P, Haldar J P, Liang Z P. Robust water/fat separation in the presence of large field inhomogeneities using a graph cut algorithm. Magn Reson Med 2010; 63(1):79-90.
5. Yu H, Shimakawa A, McKenzie C A, Brodsky E, Brittain J H, Reeder S B. Multiecho water-fat separation and simultaneous R2* estimation with multifrequency fat spectrum modeling. Magn Reson Med 2008; 60(5):1122-1134.
6. Reeder S B, Wen Z, Yu H, Pineda A R, Gold G E, Markl M, Pelc N J. Multicoil Dixon chemical species separation with an iterative least-squares estimation method. Magn Reson Med 2004; 51(1):35-45.
7. Yu H, Reeder S B, Shim akawa A, Brittain J H, Pelc N J. Field map estimation with a region growing scheme for iterative 3-point water-fat decomposition. Magn Reson Med 2005; 54(4):1032-1039.
8. Lu W, Lu Y. JIGSAW: Joint Inhomogeneity estimation via Global Segment Assembly for Water-fat separation. IEEE Trans Med Imaging 2011; 30(7):1417-1426.
9. Soliman A S, Yuan J, Vigen K K, White J A, Peters T M, McKenzie C A. Max-IDEAL: A max-flow based approach for IDEAL water/fat separation. Magn Reson Med 2013.
10. Yu H, Reeder S B, Shim akawa A, McKenzie C A, Brittain J H. Robust multipoint water-fat separation using fat likelihood analysis. Magn Reson Med 2012; 67(4):1065-1076.
11. Tsao J, Jiang Y. Hierarchical IDEAL: fast, robust, and multiresolution separation of multiple chemical species from multiple echo times. Magn Reson Med 2013; 70(1):155-159.
12. Lu W, Hargreaves B A. Multiresolution field map estimation using golden section search for water-fat separation. Magn Reson Med 2008; 60(1):236-244.
13. Jacob M, Sutton B P. Algebraic decomposition of fat and water in MRI. IEEE Trans Med Imaging 2009; 28(2):173-184.
14. Cui C, Wu X, Newell J D, Jacob M. Fat water decomposition using globally optimal surface estimation (GOOSE) algorithm. Magn Reson Med 2014.
15. Berglund J, Kullberg J. Three-dimensional water/fat separation and T2* estimation based on whole-image optimization—application in breathhold liver imaging at 1.5 T. Magn Reson Med 2012; 67(6):1684-1693.
16. Hernando D, Haldar J P, Sutton B P, Ma J, Kellman P, Liang Z P. Joint estimation of water/fat images and field inhomogeneity map. Magn Reson Med 2008; 59(3):571-580.
17. Reeder S B, Cruite I, Hamilton G, Sirlin C B. Quantitative assessment of liver fat with magnetic resonance imaging and spectroscopy. J Magn Reson Imaging 2011; 34(4):729-749.
18. Yu H, Shimakawa A, Hines C D, McKenzie C A, Hamilton G, Sirlin C B, Brittain J H, Reeder S B. Combination of complex-based and magnitude-based multiecho water-fat separation for accurate quantification of fat-fraction. Magn Reson Med 2011; 66(1):199-206.
19. Hernando D, Liang Z P, Kellman P. Chemical shift-based water/fat separation: a comparison of signal models. Magn Reson Med 2010; 64(3):811-822.
20. Liu J, Drangova M. Intervention-based multidimensional phase unwrapping using recursive orthogonal referring. Magn Reson Med 2012; 68(4):1303-1316.

Therefore what is claimed is:
1. A method of mapping of the main magnetic field (B0) of a magnetic resonance scanner, the method comprising:

receiving multiple gradient echo image data;
processing the multiple gradient echo image data to generate a magnitude-based water mask;
generating a complex data set based on selected echoes of the multiple gradient echo image data, wherein the selected echoes are selected to have an effective echo delay time that corresponds to a fat-induced phase shift that is closest to a multiple of 2*pi;
unwrapping the phase of the complex data set to obtain an initial B0 map;
calculating a bias frequency shift based on a calculated phase shift of fat during acquisition of the selected echoes and the effective echo time;
calculating a bias-corrected phase shift of fat that is produced during acquisition of the selected echoes;
employing the magnitude-based water mask to correct for a global phase error present in the initial B0 map, thereby obtaining a globally phase-error-corrected B0 map;
employing the bias-corrected phase shift of fat to correct for local phase errors in the globally phase-error-corrected B0 map, thereby obtaining a phase-error corrected B0 map;
calculating a corrected fat-fraction map based on the phase-error corrected B0 map and the bias frequency shift; and
employing the corrected fat-fraction map to perform bias removal on the phase-error corrected B0 map and generating a final B0 frequency map.

2. The method according to claim 1 wherein processing the multiple gradient echo image data to generate the magnitude-based water mask comprises:
generating a set of trial fat-fraction maps, setting a fat-fraction of all pixels equal to values between 0 and 1 for each trial fat-fraction map;
calculating a residue map for each trial fat-fraction map by:
employing a fat model to calculate a plurality of signal magnitudes, for each pixel, wherein the plurality of signal magnitudes are obtained using different relaxation rates that vary over a pre-selected range of relaxation rates; and
for each pixel, comparing the plurality of signal magnitudes to a measured signal magnitude, and selecting a relaxation rate that provides a lowest residue; and
generating a magnitude-based water map by calculating a weighted average of the fat-fraction values, wherein the lowest residues are employed to calculate the weighted average of the fat-fraction values; and
generating the magnitude-based water mask by thresholding the magnitude-based water map.

3. The method according to claim 1 further comprising generating a magnitude-based relaxation map by calculating a weighted average of the relaxation rates corresponding to the lowest residues, wherein the lowest residues are employed to calculate the weighted average of the relaxation rates.

4. The method according to claim 3 wherein the magnitude-based relaxation map is employed in the calculation of the corrected fat-fraction map.

5. The method according to claim 1 wherein the selected echoes are evenly spaced in time, and wherein the selected echoes are selected according to:

determining a multiple echo spacing corresponding to a time duration that is closest to the time period required for fat to experience a phase shift of a multiple of 2*pi;
if the multiple echo spacing is less than the total number of echoes, selecting an echo pair separated by the multiple echo spacing.

6. The method according to claim 1 wherein the selected echoes are evenly spaced in time, and wherein the selected echoes are selected according to:
determining a multiple echo spacing corresponding to a time duration that is closest in time to the time period required for fat to experience a phase shift of a multiple of 2*pi;
if the multiple echo spacing is greater than or equal to the total number of echoes, selecting more than two echoes.

7. The method according to claim 1 wherein the selected echoes are unevenly spaced in time, and wherein the selected echoes are selected by:
calculating theoretical phase shift values for a plurality of echo pairs; and
selecting an echo pair having a theoretical phase shift value that differs from a multiple of 2*pi by an amount that is less than a phase-shift threshold.

8. The method according to claim 7 wherein two or more echo pairs have theoretical phase shift values that are less than the phase-shift threshold, and wherein the echo pair that is selected has a minimum TE difference and a shortest TE value among the two or more echo pairs.

9. The method according to claim 1 wherein the complex data set is generated by calculating a Hermitian product of the signals from the selected echoes.

10. The method according to claim 1 wherein the global phase error is corrected by:
generating a plurality of trial B0 maps for correcting the global phase error, each trial B0 map being generated by phase-shifting the initial B0 map by a different trial phase shift, wherein each trial phase shift is a multiple of 2*pi;
generating, from the plurality of trial B0 maps, a plurality of trial phase-based water masks;
comparing each trial phase-based water mask to the magnitude-based water mask;
selecting, as the global phase error correction, the trial phase shift that corresponds to the trial phase-based water mask having an optimal match with the magnitude-based water mask;
thereby obtaining the globally phase-error-corrected B0 map.

11. The method according to claim 10 wherein each trial phase-based water mask is generated by:
evaluating a phase image of a Hermitian-product between adjacent echoes of the multiple gradient echo image data;
determining a corrected phase shift by subtracting, from the phase image, a B0 phase correction calculated based on the trial B0 map; and
thresholding the corrected phase shift according to a pre-selected threshold, thereby obtaining the trial phase-based water mask.

12. The method according to claim 1 wherein the local phase errors are corrected by:
dividing pixels of the globally phase-error-corrected B0 map into a plurality of first regions based on one or more phase gradient thresholds;

within each first region:
applying a set of trial phase shifts, wherein each trial phase shift is a multiple of 2*pi;
determining a corrected phase shift for each pixel;
determining the number of in-range pixels that have corrected phase shift values within in a pre-selected phase range that is bounded by the bias-corrected phase shift of fat; and
selecting, as the local phase error correction, the trial phase shift resulting in the largest ratio of in-range pixels relative to total pixels.

13. The method according to claim 12 further comprising:
identifying out-of-range pixels in that have phase values outside of the pre-selected phase range;
dividing the out-of-range pixels into a plurality of second regions;
within each second region:
applying a set of trial phase shifts, wherein each trial phase shift is a multiple of 2*pi;
determining a corrected phase shift for each pixel;
determining the number of pixels that have corrected phase shift values within in a pre-selected phase range that is bounded by the bias-corrected phase shift of fat; and
selecting, as the local phase error correction, the trial phase shift resulting in the largest ratio of in-range pixels relative to total pixels.

14. The method according to claim 13, further comprising:
generating a locally-corrected phase-based water mask after having applied the local phase error corrections to the first regions and the second regions;
comparing the locally-corrected phase-based water mask to the magnitude-based water mask and identifying unmatched pixels;
grouping the unmatched pixels into third regions;
within each third region having unmatched pixels exceeding a threshold pixel number:
applying a set of trial phase shifts, wherein each trial phase shift is a multiple of 2*pi;
determining a corrected phase shift for each pixel;
for each trial phase shift, determining the number of pixels that have phase values within in a pre-selected phase range that is bounded by the bias-corrected phase shift of fat; and
selecting, as the local phase error correction, the trial phase shift resulting in the largest ratio of in-range pixels relative to total pixels.

15. The method according to claim 12 wherein determining a corrected phase shift for each pixel comprises:
evaluating a Hermitian-product between adjacent echoes of the multiple gradient echo image data;
determining a corrected phase shift by subtracting, from the phase of the Hermitian product, a B0 phase correction calculated based on pixel phase that is shifted by the trial phase shift.

16. The method according to claim 1 wherein the multiple gradient echo image data is multi-channel image data, wherein the method comprises performing B0 mapping on each channel separately.

17. The method according to claim 1 wherein the multiple gradient echo image data is multi-channel image data, wherein the method comprises generating composite multiple gradient echo image data from two or more of the channels, and performing B0 mapping on the composite multiple gradient echo image data.

18. The method according to claim 1 wherein the multiple gradient echo image data comprises three or more echoes.

19. The method according to claim 1 wherein a multi-peak fat model is employed when calculating of any one or more of the magnitude-based water mask, the phase-error-corrected B0 map, the bias-corrected phase shift of fat, and the corrected fat-fraction map.

20. A method of mapping of the main magnetic field (B0) of a magnetic resonance scanner, the method comprising:
receiving multiple gradient echo image data;
processing the multiple gradient echo image data to generate a magnitude-based water mask;
generating a complex data set based on selected echoes of the multiple gradient echo image data, wherein the selected echoes are selected to have an effective echo delay time that corresponds to a fat-induced phase shift that is closest to a multiple of 2*pi;
unwrapping the phase of the complex data set to obtain an initial B0 map;
employing the magnitude-based water mask to correct for a global phase error present in the initial B0 map, thereby obtaining a globally phase-error-corrected B0 map;
employing a bias-corrected phase shift of fat to correct for local phase errors in the globally phase-error-corrected B0 map, thereby obtaining a phase-error corrected B0 map;
calculating a corrected fat-fraction map based on the phase-error corrected B0 map and a bias frequency shift; and
employing the corrected fat-fraction map to perform bias removal on the phase-error corrected B0 map and generating a final B0 frequency map.

21. A method of mapping of the main magnetic field (B0) of a magnetic resonance scanner, the method comprising:
receiving multiple gradient echo image data;
generating a complex data set based on selected echoes of the multiple gradient echo image data, wherein the selected echoes are selected to have an effective echo delay time that corresponds to a fat-induced phase shift that is closest to a multiple of 2*pi;
unwrapping the phase of the complex data set to obtain an initial B0 map;
correcting for a global phase error and local phase errors present in the initial B0 map, thereby obtaining a phase-error corrected B0 map;
calculating a corrected fat-fraction map based on the phase-error corrected B0 map and a calculated bias frequency shift; and
employing the corrected fat-fraction map to perform bias removal on the phase-error corrected B0 map and generating a final B0 frequency map.

22. A method of mapping of the main magnetic field (B0) of a magnetic resonance scanner, the method comprising:
receiving multiple gradient echo image data;
generating a complex data set based on selected echoes of the multiple gradient echo image data, wherein the selected echoes are selected to have an effective echo delay time that corresponds to a fat-induced phase shift that is closest to a multiple of 2*pi;
unwrapping the phase of the complex data set to obtain an initial B0 map;
correcting for a global phase error and local phase errors present in the initial B0 map, thereby obtaining a phase-error corrected B0 map; and
performing bias removal on the phase-error corrected B0 map and generating a final B0 frequency map.

23. A method of mapping of the main magnetic field (B0) of a magnetic resonance scanner, the method comprising:
receiving multiple gradient echo image data;
generating a complex data set based on selected echoes of the multiple gradient echo image data, such that the complex data set is a pseudo-in-phase complex data set;
unwrapping the phase of the complex data set to obtain an initial B0 map;
correcting for a global phase error and local phase errors present in the initial B0 map, thereby obtaining a phase-error corrected B0 map; and
performing bias removal on the phase-error corrected B0 map and generating a final B0 frequency map.

24. A magnetic resonance imaging system comprising:
a magnetic resonance scanner; and
computing hardware operatively connected to said magnetic resonance scanner, said computing hardware comprising a processor coupled to a memory, wherein the processor, in response to executing instructions stored in the memory, is configured to:
process multiple gradient echo image data to generate a magnitude-based water mask;
generate a complex data set based on selected echoes of the multiple gradient echo image data, wherein the selected echoes are selected to have an effective echo delay time that corresponds to a fat-induced phase shift that is closest to a multiple of 2*pi;
unwrap the phase of the complex data set to obtain an initial B0 map;
calculate a bias frequency shift based on a calculated phase shift of fat during acquisition of the selected echoes and the effective echo time;
calculate a bias-corrected phase shift of fat that is produced during acquisition of the selected echoes;
employ the magnitude-based water mask to correct for a global phase error present in the initial B0 map, thereby obtaining a globally phase-error-corrected B0 map;
employ the bias-corrected phase shift of fat to correct for local phase errors in the globally phase-error-corrected B0 map, thereby obtaining a phase-error corrected B0 map;
calculate a corrected fat-fraction map based on the phase-error corrected B0 map and the bias frequency shift; and
employ the corrected fat-fraction map to perform bias removal on the phase-error corrected B0 map and generating a final B0 frequency map.

* * * * *